US005201726A

United States Patent [19]

Kirkham

[11] Patent Number: 5,201,726

[45] Date of Patent: Apr. 13, 1993

[54] EYE-BATHING DEVICES

[75] Inventor: Clive Kirkham, Folkestone, United Kingdom

[73] Assignee: Hans Rohl, Kent, England

[21] Appl. No.: 623,804

[22] PCT Filed: Jun. 23, 1989

[86] PCT No.: PCT/GB89/00707

§ 371 Date: Jan. 30, 1991

§ 102(e) Date: Jan. 30, 1991

[87] PCT Pub. No.: WO89/12434

PCT Pub. Date: Dec. 28, 1989

[30] Foreign Application Priority Data

Jun. 24, 1988 [GB] United Kingdom ................. 8815155

Nov. 24, 1988 [GB] United Kingdom ................. 8827421

[51] Int. Cl.[5] ............................................. A61M 35/00

[52] U.S. Cl. .................................... 604/294; 604/297; 604/301; 604/310; 222/383; 222/318

[58] Field of Search ............... 604/289, 294, 295, 296, 604/301, 310, 297, 298, 299, 300; 128/65, 66; 222/383, 402.13, 318, 108, 424, 183

[56] References Cited

U.S. PATENT DOCUMENTS

| | | | |
|---|---|---|---|
| 1,121,667 | 12/1914 | Ross | 604/297 |
| 1,362,682 | 12/1920 | Dayton | 604/297 |
| 2,524,720 | 10/1950 | Watrous | 604/301 X |
| 2,754,821 | 7/1956 | Burbig et al. | 604/301 X |
| 2,826,194 | 3/1958 | Golden . | |
| 3,261,355 | 7/1966 | Burbig | 604/301 X |
| 3,314,426 | 4/1967 | Carroll | 604/301 X |
| 3,602,217 | 8/1971 | Felton et al. | 604/301 X |
| 3,917,119 | 11/1975 | Kahn | 604/301 X |
| 4,131,115 | 12/1978 | Peng . | |
| 4,641,384 | 2/1987 | Landsberger et al. | 4/620 |
| 4,740,206 | 4/1988 | Allander | 604/294 |
| 4,758,237 | 7/1988 | Sacks | 604/254 |
| 4,798,599 | 1/1989 | Thomas | 604/290 |
| 4,892,526 | 1/1990 | Reese | 604/290 |
| 4,902,281 | 2/1990 | Avoy | 604/191 |
| 5,030,214 | 7/1991 | Spector | 604/301 |
| 5,133,701 | 7/1992 | Han | 604/289 |
| 5,133,702 | 7/1992 | Py | 604/302 |

FOREIGN PATENT DOCUMENTS

| | | | |
|---|---|---|---|
| 626132 | 12/1962 | Belgium | 604/297 |
| 295162 | 11/1916 | Fed. Rep. of Germany | 604/297 |
| 2744654 | 4/1978 | Fed. Rep. of Germany . | |
| 34504 | 3/1922 | Norway | 604/297 |
| 561985 | 6/1944 | United Kingdom | 604/295 |
| 867904 | 5/1961 | United Kingdom | 604/301 |
| 2048074 | 12/1980 | United Kingdom | 604/297 |
| 8702237 | 4/1987 | World Int. Prop. O. . | |

*Primary Examiner*—C. Fred Rosenbaum
*Assistant Examiner*—Mark O. Polutta
*Attorney, Agent, or Firm*—Pollock, Vande Sande & Priddy

[57] ABSTRACT

An eye-bathing device comprises an eye-cup (14) adapted to receive the eye being bathed, and a pump (11) for delivering an eye bathing solution to the eye-cup through a spray nozzle (13), the eye-cup (14) having an inlet opening (35) aligned with the spray nozzle. The pump (11) is hand-operated, and is located within a housing (10) supporting the eye-cup (14).

14 Claims, 4 Drawing Sheets

EYE-BATHING DEVICES

This invention relates to an eye-bathing device for applying solutions to the eyes.

A simple eye bath consists of a moulded plastic cup which is filled with solution and held tight to the eye. In use, the head is first tilted back to immerse the eye in the solution and is then moved from side to side to wash the eye. Disabled persons having restricted head movement therefore find eye baths particularly difficult to use.

A further serious disadvantage of the simple eye bath is that the washing solution itself can become contaminated with the irritant removed from the eye.

A more complex eyewash system for industrial use is disclosed in U.S. Pat. No. 4,641,384. In this case the entire face of the user is postioned within a hood, and a pivotable spray nozzle is adjusted to direct a spray of liquid into the eye or eyes in response to actuation of a battery-operated pump. With such a system, the user has no control over the force of the spray and it is difficult to ensure that the spray travels in the required direction. The system is also bulky and generally unsuited for domestic use.

There is therefore a need for an improved device which overcomes the drawbacks of the simple eye-bath while remaining relatively inexpensive and easy to use.

According to the present invention there is provided an eye-bathing device comprising an eye-cup adapted to receive the eye being bathed, and a pump for delivering an eye-bathing solution to the eye-cup through a spray device, the eye-cup having an inlet opening aligned with the spray device. In a preferred embodiment, the pump is hand-operated and is located within a housing supporting the eye-cup. A particular advantage of this arrangement is that the user is able to control the force of the spray by varying the pressure applied to the pump. Moreover, by directing the spray into an eye-cup, it is no longer necessary to adjust the position of the spray nozzle to ensure that the spray reaches the eye.

The eye-cup is preferably supported by the housing in a tilted back orientation and includes a first outlet through which waste solution drains to a sump and a second outlet providing an air vent. The device preferably includes a base releasably engageable with the housing to form a free-standing structure.

A reservoir of the eye-bathing solution is preferably stored in a refill container which is detachable from the pump and also lies within the housing.

By way of example only, an embodiment of the invention is illustrated in the accompanying drawings in which.

Figure 1:
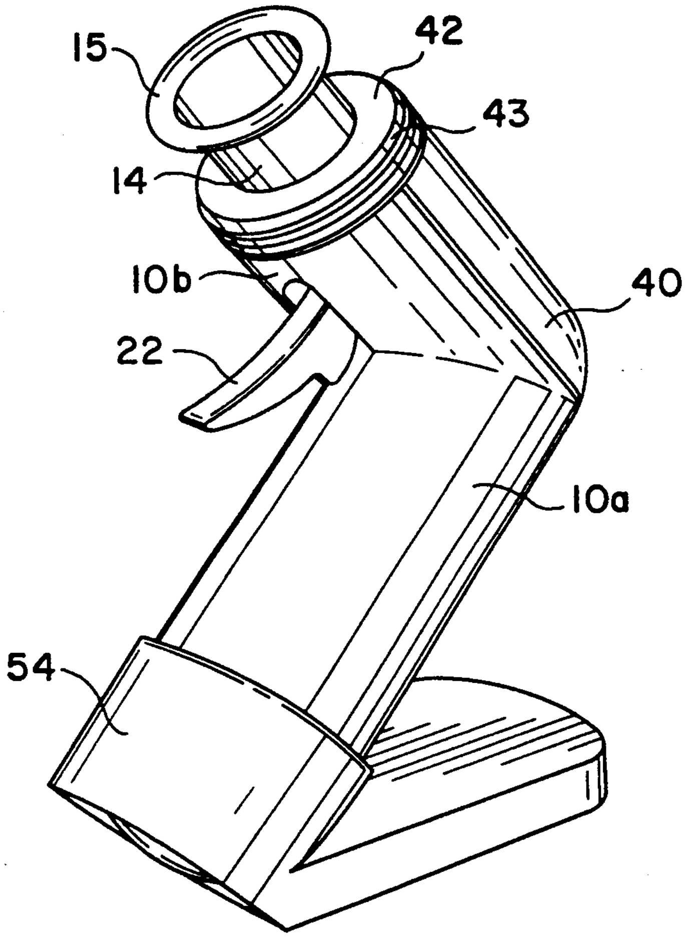
FIG. 1 is a perspective view of an eye-bathing device.
Figure 2:
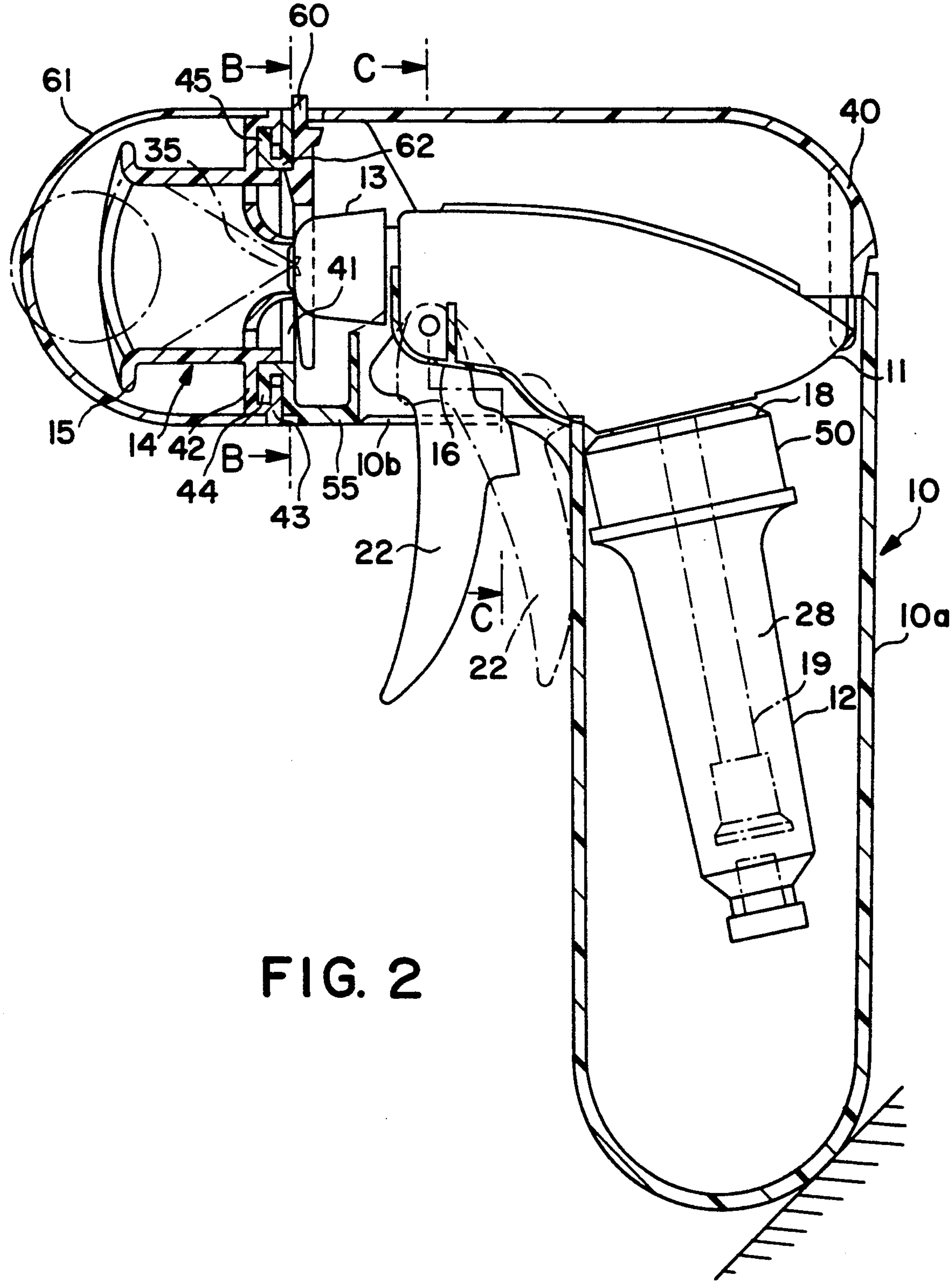
FIG. 2 is a schematic side view of the device shown in FIG. 1 when removed from its base and showing some of the internal components.

Referring to these drawings, the device consists of an L-shaped housing 10 containing an hand-operated pump 11 which delivers an eye-bathing solution from a reservoir 28 to a spray nozzle 13. The housing 10 is releasably engageable with a base 54 to form a free-standing structure, and is moulded with a detachable cover 40. The cover 40 is detached by pulling back a flap 60 to release a catch 62.

An eye-cup 14 is releasably engaged in an opening 41 at the front of the housing 10, the nozzle 13 being aligned with an opening 35 in the base of the cup 14. The cup 14 is formed of a softer material than the housing 10, and has a flexible sealing rim 15 which fits around the eye.

The eye-cup 14 is engaged in the opening 41 by means of an outwardly projecting flange 42 having a peripheral lip 43 formed with an inwardly directed groove 44 adapted to receive an outwardly projecting tongue 45 bounding the opening 41. The resilience of the material forming the eye-cup is such that the peripheral lip 43 can be deformed outwards to release the engagement between the eye-cup and the housing.

When not in use, the eye-cup 14 is protected by a removable dust cap 61.

The body of the pump 11 is supported and retained within a central hollow area of a forwardly projecting base portion **10*b* of the housing 10, the hollow area being bounded by internal walls 16 level with the side split between the cover 40 and the base 10*b* of the housing. A refill container 12 containing the reservoir 28 of eye-bath solution is releasably secured to the body of the pump and lies wholly within the housing 10. In this particular example, the container 12 has an internally screw threaded mouth 50 which engages a screw threaded ring 18 secured to the body 11 of the pump. A pick-up tube 19 extends from the inlet of the pump into the reservoir 28 and, during the suction stroke of the pump, air is drawn into the container 12** through the screw threaded coupling at the junction between the container and the pump body.

Figure 3:
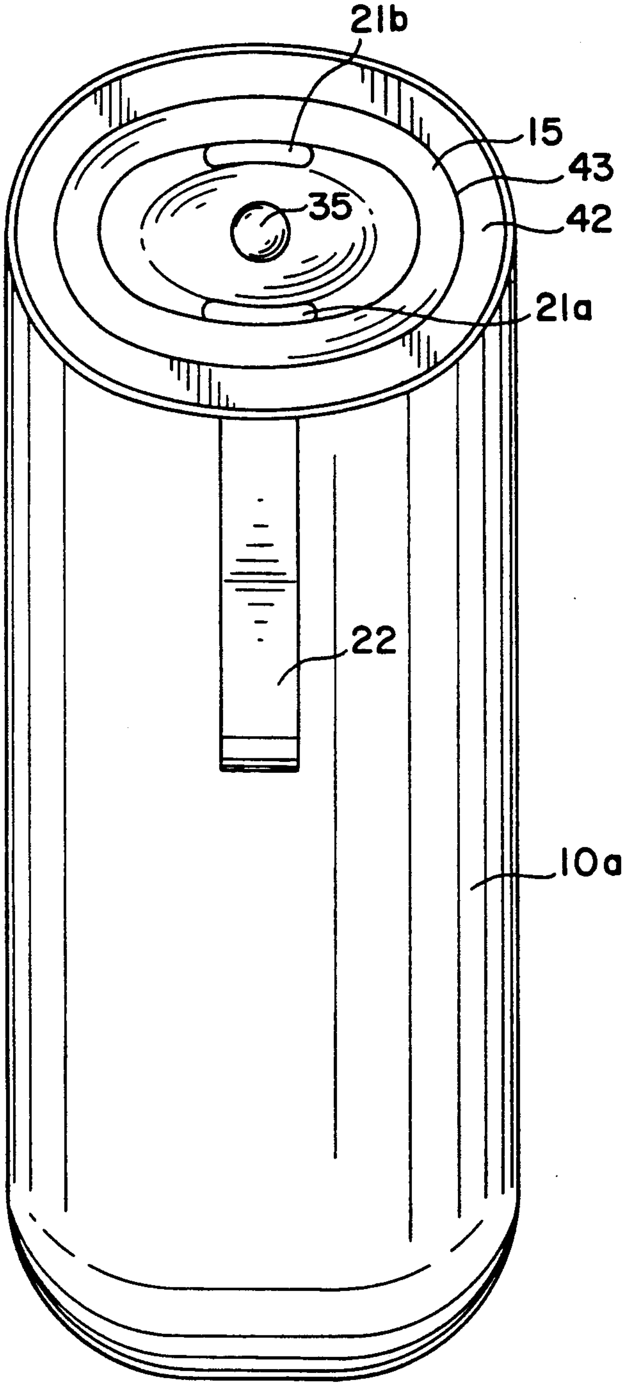
FIG. 3 is a front view of the device.
Figure 4:
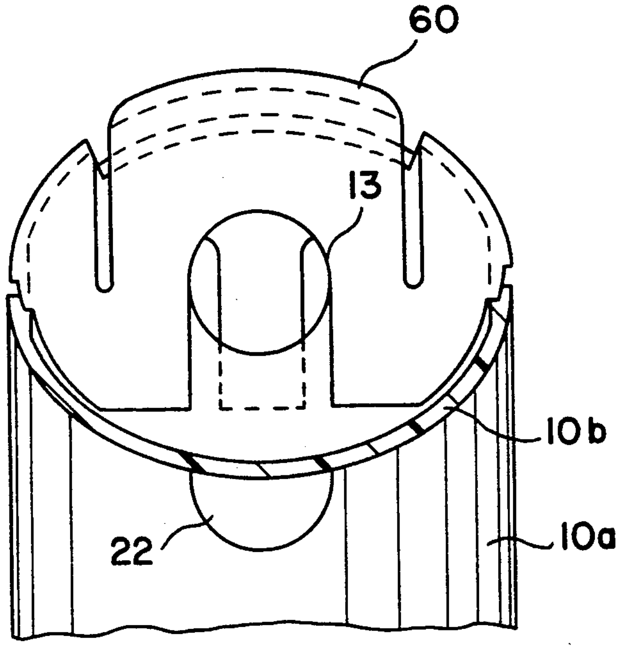
FIG. 4 is a section on line B—B of FIG. 2.
Figure 5:
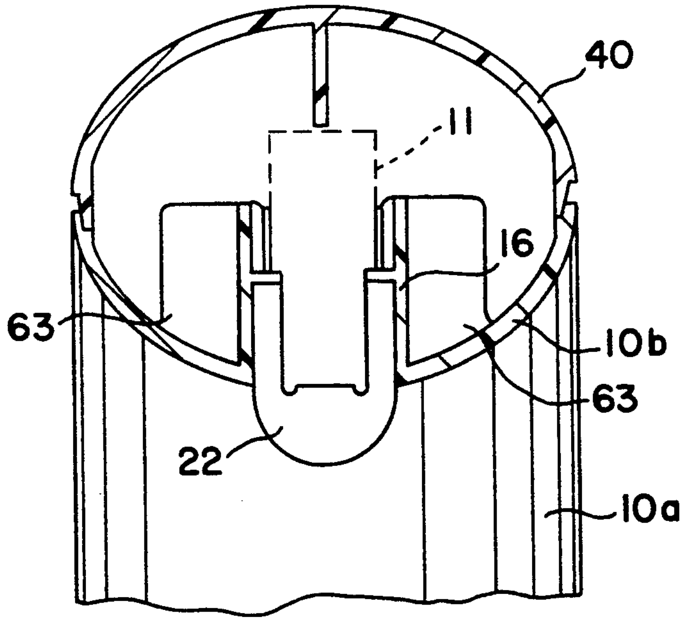
FIG. 5 is a section on line C—C of FIG. 2.

The downwardly inclined portion **10*a* of the L-shaped housing 10 forms a sump for receiving waste solution which drains internally through the housing 10 from a drain hole 21*a* (FIG. 3) located in the base of the eye-cup 14 adjacent and beneath the nozzle opening 35. A similar opening 21*b* located above the nozzle opening 35 provides an air vent, the symmetrical location of the two openings 21*a*, 21*b* ensuring that the eye-cup will function equally well when inverted. With the housing 10 located in its base 54, the eye-cup 14 is tilted backwards such that waste solution which collects in the cup automatically empties through the drain hole 21. The waste runs in channels 63 around the outside of the internal walls 16 supporting the pump 11 and its actuating lever 22** so that there is no risk of the solution comming into contact with the user.

The hand-operated pump 11 includes an actuating lever 22 which projects through a slot in the housing 10 within the area bounded by the internal walls 16. The pump operates in a well-known manner and is not therefore described or illustrated in detail. Briefly, depression of the lever 22 urges a piston along a cylinder against the bias of a spring, the cylinder having inlet and outlet ports with respective inlet and delivery valves communicating with the reservoir 28 and the spray nozzle 10 respectively. During the pressure stroke, solution 28 is pumped from the cylinder along a discharge tube to the spray nozzle 13, and fresh solution is then drawn into the cylinder from the reservoir 28 during the return or release stroke.

The nozzle 13 discharges the solution into the eye-cup 14 as a fine mist or spray. Advantageously, the force of the spray can be regulated by varying the pressure applied to the lever 22. Moreover, internal drainage of the waste solution to the sump **10*a* has a twofold advantage. Firstly it prevents the waste solution from coming into contact with the user, and secondly it prevents fresh washing solution from becoming contaminated with the irritant removed from the eye. Integral internal shoulders or ribs 55 in the forwardly projecting portion 10*b* of the housing 10 ensure that waste solution is directed clear of the slot for the actuating lever 22**.

The eye-cup 14 is easily cleaned by removing it from the housing 10.

With the housing 10 being a simple push-fit in the base 54 the device is easy to assemble and comfortable to use. With the base 60 resting on a support surface at a comfortable height, the user merely inclines his head toward the eye-cup 14, as if he were looking into a microscope.

When not in use, the rearwardly inclined portion **10*a* of the housing 10 can be removed from the base 54, turned through 180°, and re-engaged with the base so that the portion 10*b*** of the housing projects downwards instead of upwards. This is useful for packing and storing the device.

Each actuation of the lever 22 delivers a fresh sterile solution to the eye-cup so that the device is particularly hygienic and could be used, for example, in eye hospitals or casualty wards. The user has merely to blink his eyes in the fine spray or mist to provide a thorough cleansing action, the waste solution being continuously drained to the sump **10*a*. The sump is easily emptied whenever necessary by removing the cover 40 and inverting the housing 10**.

In one alternative embodiment (not illustrated), the pump 11 delivers solution to a pair of spray nozzles each having an associated eye-cup, the components being otherwise substantially identical to those shown in the illustrated embodiment.

I claim:

1. An eye-bathing device comprising an eye cup supported by a housing and adapted to receive the eye being bathed, a hand-operated pump mounted within a first portion of said housing, said pump having a pivotally-mounted actuating lever projecting through an aperture in said first portion of said housing for delivering an eye-bathing solution from a separate reservoir connected to said pump in said housing to the eye cup through a spray device, and a sump formed in a second portion of said housing, said first portion of the housing having an internal passage for draining waste solution from a first outlet of the eye cup to said sump.

2. A device according to claim 1 in which a removable coner is detachable from the housing to permit emptying of the sump.

3. A device according to claim 1 or 2 in which said sump is formed by an external wall of the housing.

4. A device according to claim 1 in which said internal passage is formed by an external wall of said first portion of said housing and an internal wall on which the actuating lever is mounted.

5. A device according to claim 1 or claim 2 in which the eye cup is detachable from said first portion of said housing.

6. A device according to claim 1 or 2 in which the eye cup includes a second outlet providing an air vent.

7. A device according to claim 6 in which the first and second outlets are located such that, with the eye cup rotated through 180°, the two outlets interchange their positions.

8. A device according to claim 1 or claim 2 in which the housing is hand-held, and further comprising a base releasably engageable with the second portion of the housing to form a free-standing structure.

9. A device according to claim 8 in which the second portion of the housing extends rearwardly and upwardly from the base and the first portion of the housing projects forwardly and upwardly from the top of the second portion, the eye cup forming a closure at the forwardmost end of the first portion.

10. A device according to claim 9 in which the housing is engageable with the base in an alternative non-operative orientation wherein said first portion of the housing is turned through 180° and projects downwardly and rearwardly toward the base.

11. A device according to claim 1 or claim 2 further comprising a refill container for storing a reservoir of the solution, the container being detachable from the pump and lying within said second portion of said housing.

12. An eye bathing device comprising:

a first housing portion open at first and second ends, including a pump connected to a reservoir, said pump having an actuator trigger extending through said first housing portion and including a spray nozzle for directing pumped eye wash through said first end;

an eye cup having a rear surface supported in said first end of said first housing portion, said rear surface having an opening aligned with said spray nozzle, and a drain hole and vent hole in communication with said first housing portion; and, a second housing portion having a first open end connected to said first housing portion open second end, forming a sump for collecting eye wash flowing through said drain hole into said first housing portion.

13. The eye bathing device of claim 12 wherein said eye cup is detachably connected to said first housing portion.

14. The eye bathing device of claim 12 wherein said reservoir extends through said first housing portion second end into said second housing portion, making said reservoir accessible when a removable cover is detached from said first housing portion and said second housing portion.

* * * * *